United States Patent
Ellingsen et al.

(10) Patent No.: US 7,276,028 B2
(45) Date of Patent: Oct. 2, 2007

(54) SENSOR IN VIVO MEASUREMENT OF OSMOTIC CHANGES

(75) Inventors: Olav Ellingsen, Florø (NO); Bård Erik Kulseng, Trondheim (NO); Helge Kristiansen, Oslo (NO)

(73) Assignee: Lifecare AS, Bergen (NO)

( * ) Notice: Subject to any disclaimer, the term of this patent is extended or adjusted under 35 U.S.C. 154(b) by 48 days.

(21) Appl. No.: 10/559,323

(22) PCT Filed: Jun. 9, 2004

(86) PCT No.: PCT/NO2004/000166

§ 371 (c)(1),
(2), (4) Date: Mar. 31, 2006

(87) PCT Pub. No.: WO2004/107972

PCT Pub. Date: Dec. 16, 2004

(65) Prior Publication Data

US 2006/0173252 A1    Aug. 3, 2006

(30) Foreign Application Priority Data

Jun. 10, 2003    (NO) .................................. 20032608

(51) Int. Cl.
*A61B 5/00*    (2006.01)
(52) U.S. Cl. ..................................................... 600/309
(58) Field of Classification Search ................ 600/309, 600/310, 316, 365
See application file for complete search history.

(56) References Cited

U.S. PATENT DOCUMENTS

| | | | |
|---|---|---|---|
| 4,385,636 A * | 5/1983 | Cosman ....................... 600/561 |
| 4,538,616 A * | 9/1985 | Rogoff ........................ 600/365 |
| 4,718,430 A * | 1/1988 | Holzer ........................ 600/365 |
| 4,773,269 A | 9/1988 | Knecht et al. | |
| 5,337,747 A | 8/1994 | Neftel | |
| 5,388,449 A * | 2/1995 | LeVeen et al. ............. 73/64.47 |
| 6,546,268 B1 | 4/2003 | Ishikawa et al. | |

FOREIGN PATENT DOCUMENTS

| | | |
|---|---|---|
| WO | WO 03/061475 A1 | 7/2003 |
| WO | WO 2004/107972 A1 | 12/2004 |

* cited by examiner

*Primary Examiner*—Eric Winakur
*Assistant Examiner*—Etsub D Berhanu
(74) *Attorney, Agent, or Firm*—Welsh & Katz, Ltd.

(57) ABSTRACT

The present invention teaches a method, system and units for measuring changes in blood during a longer period of time in vivo with a patient by measuring diffusivity of solvent. A differential pressure sensor is arranged on a silicon wafer or beam comprising resistors being in communication with fluids in two chambers via semipermeable membranes enabling measuring of two components in said blood by tracking changes over time.

6 Claims, 6 Drawing Sheets

SENSOR IN VIVO MEASUREMENT OF OSMOTIC CHANGES

FIELD OF THE INVENTION

The present invention is related to an invasive sensor which can be implanted subcutaneously, and specially to an invasive sensor comprising at least one differential pressure-transducer that measures the pressure difference between two fluid volumes confined by, in one end the at least one differential pressure-transducer, and in the other end osmotic membranes, as defined in the enclosed independent claims.

The design and production of differential pressure sensors based on silicon micro-mechanics is known. The Norwegian company SensoNor has developed a technique for buried piezoresistors. Besides offering excellent long-term stability, this technique allows contact with water on both sides of the membrane. Using anodic or fusion bonding, hermetically sealed cavity structures can be obtained Porous etching (anodic oxidation) of silicon is also a well-known technique. Porous silicon (PS) is made by electrochemical etching of a silicon wafer in solutions containing hydrofluoric acid (HF). Usually, HF is sold in an aqueous solution with up to 50% of HF. Thus, the first attempts to form porous silicon were performed using only HF diluted in de-ionised and ultra-pure water. Due to the hydrophobic character of the clean Si surface, absolute ethanol is usually added to the aqueous solution to increase the wettability of the PS surface. So far this technique is mainly used for making visible photoluminescence (PL).

The sol-gel techniques are well known processes, used for a variety of different commercial applications, ranging from optical and electrical coatings to improve the scratch resistance.

U.S. Pat. No. 5,337,747 by Frédéric Neftel, Jan. $7^{th}$, 1993, discloses an implantable device for estimating the level of glucose in the blood by the use of osmosis.

The U.S. Pat. No. 5,337,747 is based on the use of two pressure sensors, each sensor measuring the pressure in a corresponding "chamber". This means that the signal of interest is the difference between the two sensors. This will significantly decrease both the sensitivity and accuracy of the measurement.

The pressure sensors are based on a pressure sensor where the deflection of a pressure sensitive membrane is measured by the change in the electrical capacitance between this membrane (which doubles as an electrode) and a fixed electrode. This type of sensor excludes the use of a differential element as long as the medium where the measuring of the pressure is conducted, is conductive (as in the present case where water is used).

BACKGROUND OF THE INVENTION

It should also be noted that the sensor element described in the U.S. Pat. No. 5,337,747 would not work according to its intentions. This is caused by the fact that more than 99% of the capacitance measured will be caused by the mounting between the membrane (10) and the other electrode (12) which is fixed and is not changing with changing pressure in the chamber. Less than 1% of the total capacitance will be modulated by the deflection of the pressure sensitive membrane.

In the U.S. Pat. No. 5,337,747 it is stated that one of the osmotic membranes should be permeable for water, ions and lactic acid, but not for glucose. This should be obtained by designing pores with a diameter of between 0,6 and 0,74 nm. However, this model for membrane behaviour is over-simplified and does not take into account other important effects contributing to the transport properties of the membrane. A membrane with such a cut-off (pore diameter) will not avoid osmotic effects from the stated solutes. This is because both electrical and steric effects will impede and possibly totally stop the transport of solutes. This means that it is impossible to obtain an osmotic pressure from glucose only.

U.S. Pat. No. 6,224,550, by one of the present inventors, May 1, 2001, relies on maintaining a similar osmolality on both sides of an osmotic membrane. This is obtained by allowing water to flow freely through the membrane and thereby changing the volume (and thereby the concentration) of the "calibrated" fluid inside the sensor. One of the disadvantages with this design is the fact that a significant amount of water must be transported through the membrane when the osmolality in the body is changing. However, only limited fluxes are possible through such membranes, which means that a relatively large area of the osmotic membrane is needed. In addition, the time response will depend on the actual position of a piston, and as such, the sensor will also be non-linear.

Another problem is the friction between the moving piston and the wall. To be able to move the piston, the pressure force must exceed the friction force. From measurements it is seen that even with a large cylinder radius, it is needed a high difference in osmotic pressure to move the piston, which is very unfavourable from the point of accuracy.

A more fundamental problem with this sensor is the fact that to obtain a "calibrated" fluid, the small electrolytes must be allowed to pass through the membrane. As glucose and larger molecules are excluded from passing through the membrane, the "calibrated" fluid will always have to maintain a higher concentration of the electrolytes (chlorine, potassium, etc). The result is an unstable element, from which the electrolytes gradually will be drained out, and in the end the calibrated fluid will disappear.

Osmosis

The principle of the sensor according to the present invention is based on osmosis. In its simplest form, osmosis is the transport of a solvent across a semipermeable membrane caused by differences in the concentration of solutes on either side of the membrane. Osmosis is a process where certain kinds of molecules in a liquid are preferentially blocked by a "semipermeable" membrane. The solvent (in our case water) is diffusing through the membrane into the more concentrated solution, more so than in the opposite direction. The result is a combination of two effects. One is that an osmotic (hydrostatic) pressure is built up in the volume of higher concentration. The other is the reduction in the concentration difference caused by the increased volume of solvent.

Ultimately, a dynamic equilibrium is reached, in which the increase in chemical potential caused by the osmotic pressure difference (□), equals the corresponding change caused by the difference in concentration (C). At osmotic equilibrium, the chemical potential of the solvent must equate the chemical potential of the pure solvent. The ratio between change in pressure versus change in concentration depends on the compliance of the volumes and can be changed (and optimised) by the design.

Osmotic pressure is one example of a colligative property, that is a property which depends only on the number of solute molecules, and not on the nature of the molecules. For relatively small concentrations, as those observed in the body, the osmotic pressure is equal to the pressure that the solute molecules would exert given they were in a gas of the same concentration.

$$\Pi = i\frac{RT}{V}$$

Where V is the volume of solution containing one mole of solute. The constant i, is the "van't Hoff factor", which is a measure of the relative increase in amount of entities (particles) due to dissociation.

The present invention can be utilised to monitor any changes within the in chemistry in vivo. The type of solutes and their concentration observed in vivo gives a tremendous amount of information regarding the physiology of the body, and its condition. By measuring the composition for instance in the interstitial fluid (ISF), a lot of information can be obtained regarding de-hydration of the body and different diseases. These are amongst others: diabetes, kidney function etc. Also normal variations for instance in lactate concentration caused by physical activity can be monitored.

In addition to the substances mentioned above, which can change the osmolality in the body, one can also find substances by medication, which give an osmotic contribution in the body fluid. In this case, the present invention can be used to monitor the amount of medication.

Measurement of glucose in ISF is becoming recognised as an alternative to measuring the glucose directly in the blood. The glucose measurement in blood is associated with several drawbacks. It needs a sample of blood, drawn from the body. Even though the equipment has become more sensitive, and therefore requires less blood, the process is associated with pain and the number of tests typically limited to less than 10 per day. It is also known that large variations in measured values can be caused by the measurement procedure.

The present invention is concerned with a variety of parameters like de-hydration, lactic-acid, and amino-acids in addition to glucose.

SUMMARY OF THE INVENTION

In examples of embodiments of the present invention the use of one pressure sensor of the differential type, which directly measure the difference between the two chambers, will increase the sensitivity and accuracy by order of magnitudes.

In examples of embodiments of the present invention, a piezo-resistive element, in which the sensing resistors are "buried" into the silicon, and do therefore not get into contact with the liquid in the reference volumes are used. The buried resistors can be part of a Wheatstone bridge.

GENERAL DESCRIPTION

The total sensor consists of two main parts. The first part is the sensing apparatus, which is placed inside the human (or animal) body. The other part is the control unit, which receives the sensor signal, converts it to the concentration of the solute, with the possibility of storing and displaying the real-time as well as average values.

DETAILED DESCRIPTION OF THE PREFERRED EMBODIMENTS

The sensing apparatus consists of the following elements: The sensing device, a radio transmitter (possibly a transceiver) and an energy supply, which could be a battery or an antenna for magnetic induction (see FIGS. 6A and 6B).

Sensing Device

In the present invention, the sensing device comprises the following elements. One or more differential pressure-transducers, each of which is able to directly measure the pressure difference between two liquid volumes hereafter called reference volumes. These reference volumes are internal to the osmotic sensor, and are confined by, in one end the differential pressure transducer, and in the other end the respective osmotic membranes.

A change in the glucose concentration in vivo has two effects. One is the direct change in the osmolality of the ISF. The other is a change in fluid composition (without necessary changing the total concentration of osmotic active substances). Both these effects have to be measured, as the body will be inclined to maintain a constant osmolality by slowly adjusting the concentration of the electrolytes.

Differential Measurement

Changes in the chemical composition in vivo is a combination of A) Direct changes in the osmolality of the fluid, which are directly reflected by the sensor. B) Changes in fluid composition (without changing the total concentration of osmotic active substances). The main difficulty when using osmotic techniques is to obtain an adequate specificity (the ability to distinguish between the different osmotic components).

Figure 1:
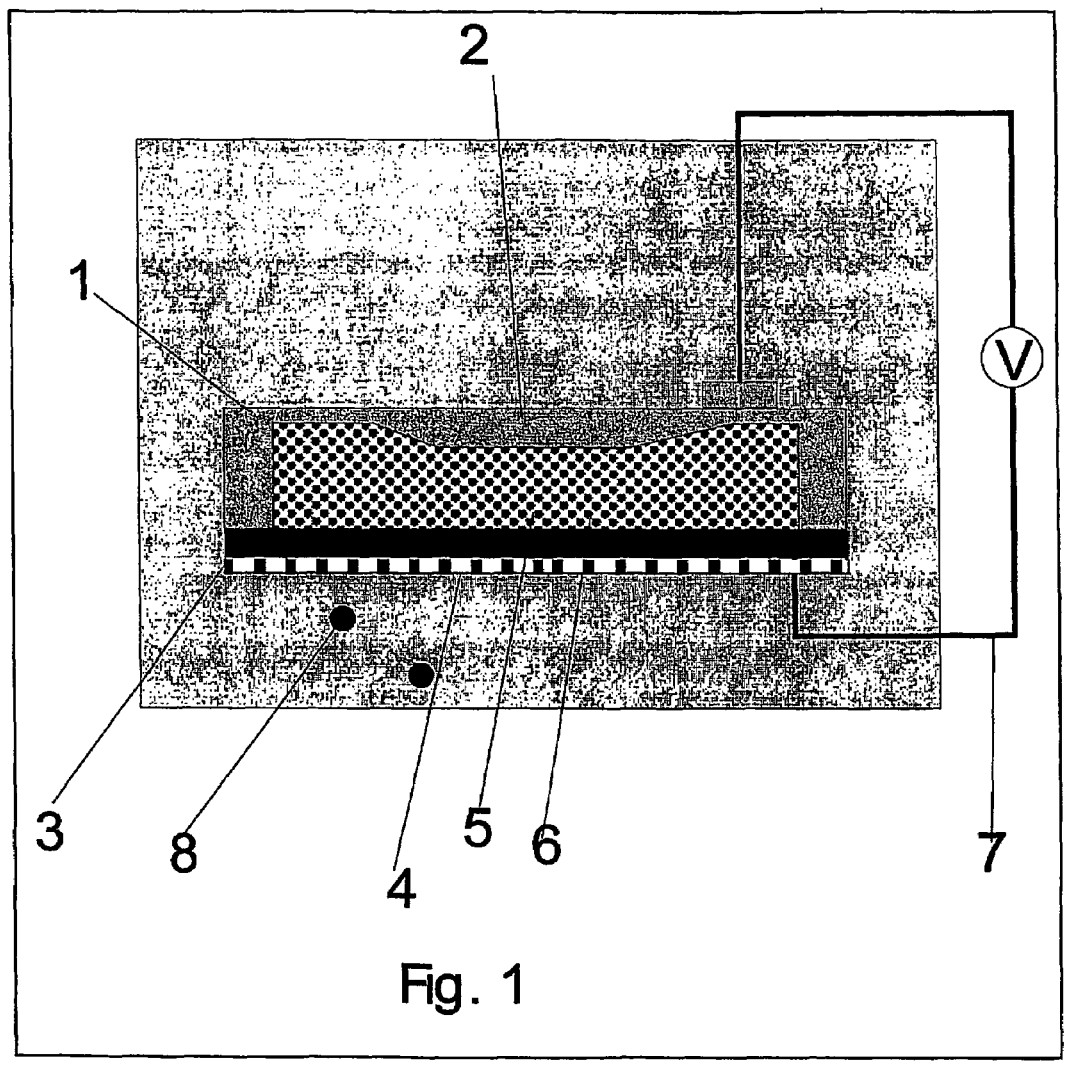
FIG. 1 illustrates an example of embodiment of the present invention.

FIG. 1 illustrates an example of embodiment according to the present invention. A sensor housing 1 made in silicon comprises a sensor 2 which is a pressure transducer or a variable capacitor that will register a change in the pressure caused by a variable flux of water inn or out of the membrane and/or a change in volume hat activates the sensor 2. A charged membrane 3 comprising both anion and cation charges are supported by a perforated support 4. A callibrated fluid 5 is present in the porous substance 6, where the osmolality is defined by the content of molecules. The fluid will normally be water while the solute is salt or for example glucose or other types of molecules. A normal condition is when the osmolality is equal on both sides of the membrane. When charged substances 8 are close to the membrane, two effects will arise. The first one is that the osmolality of the body fluid will increase which causes water to be forced out of the sensor which reduces the fluid volume in the sensor. The second effect is to change the electrical potential in the membrane due to the charges. This is illustrated with the circuit 7. A normal fluid condition provides a defined voltage over the membrane. When the ion concentration increases the voltage will change according to the negative or positive charges, and the detected difference and the osmolality changes will be proportional to the ion concentration in the fluid, and it will indicate if the registered osmolality is due to glucose or lactates.

Figure 2:
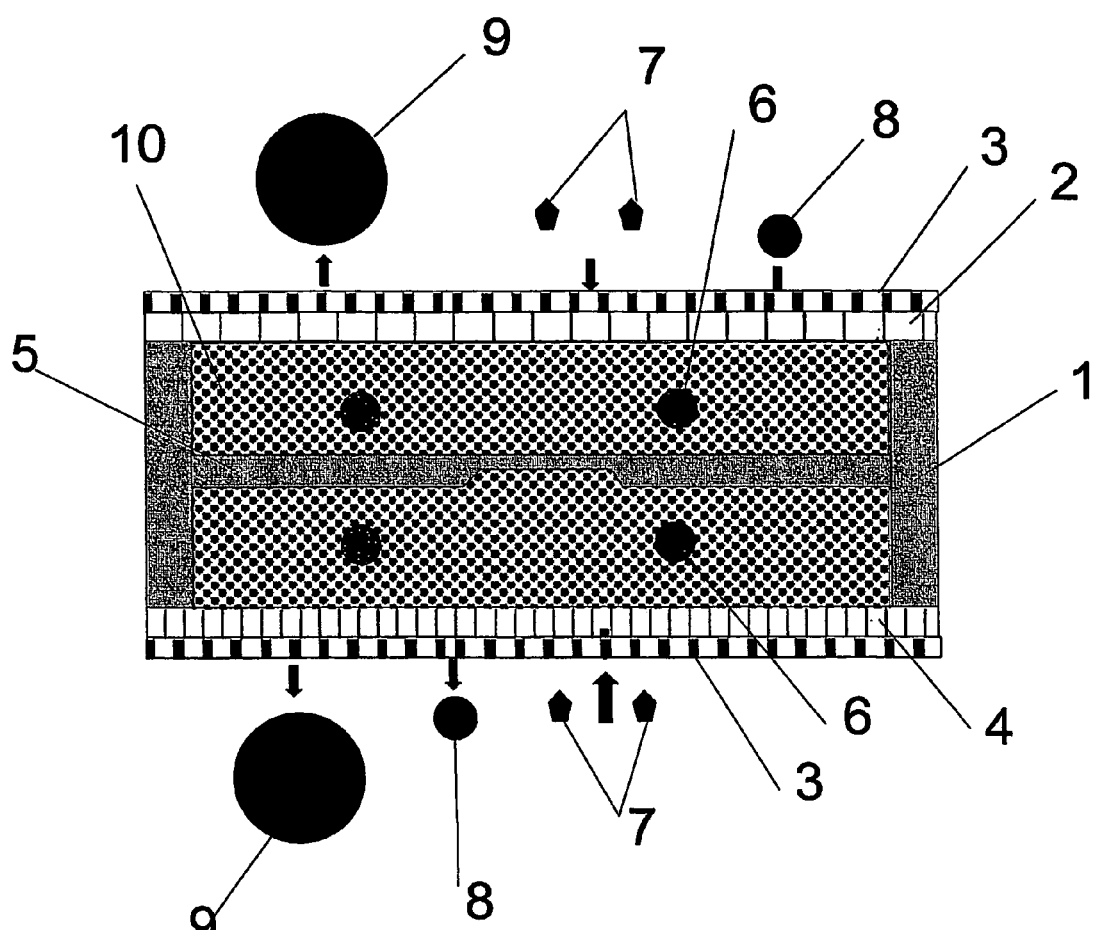
FIG. 2 illustrates another example of embodiment of the present invention.

FIG. 2 illustrates another embodiment of the present invention where there are arranged two membranes 2 and 4 on each side of the sensor housing 1. The membrane 2 has a cut-off enabling diffusion of glucose or lactions 7 in a reference fluid 6, butt hat will cut off larger molecules. The membrane 4 has a cur-off that gives an osmotic effect for glucose molecules 8, butt hat reduces or has no osmotic effect for lactions 7. The cavity above the sensor 5 provides two separate chambers filled with a porous material preferred to be an inert metal, ceramics or plastic that support the membranes from the side that faces the reference chambers. Above each membrane is arranged a stiff perforated plate 3 made of metal, ceramics or plastic.

Figure 3:
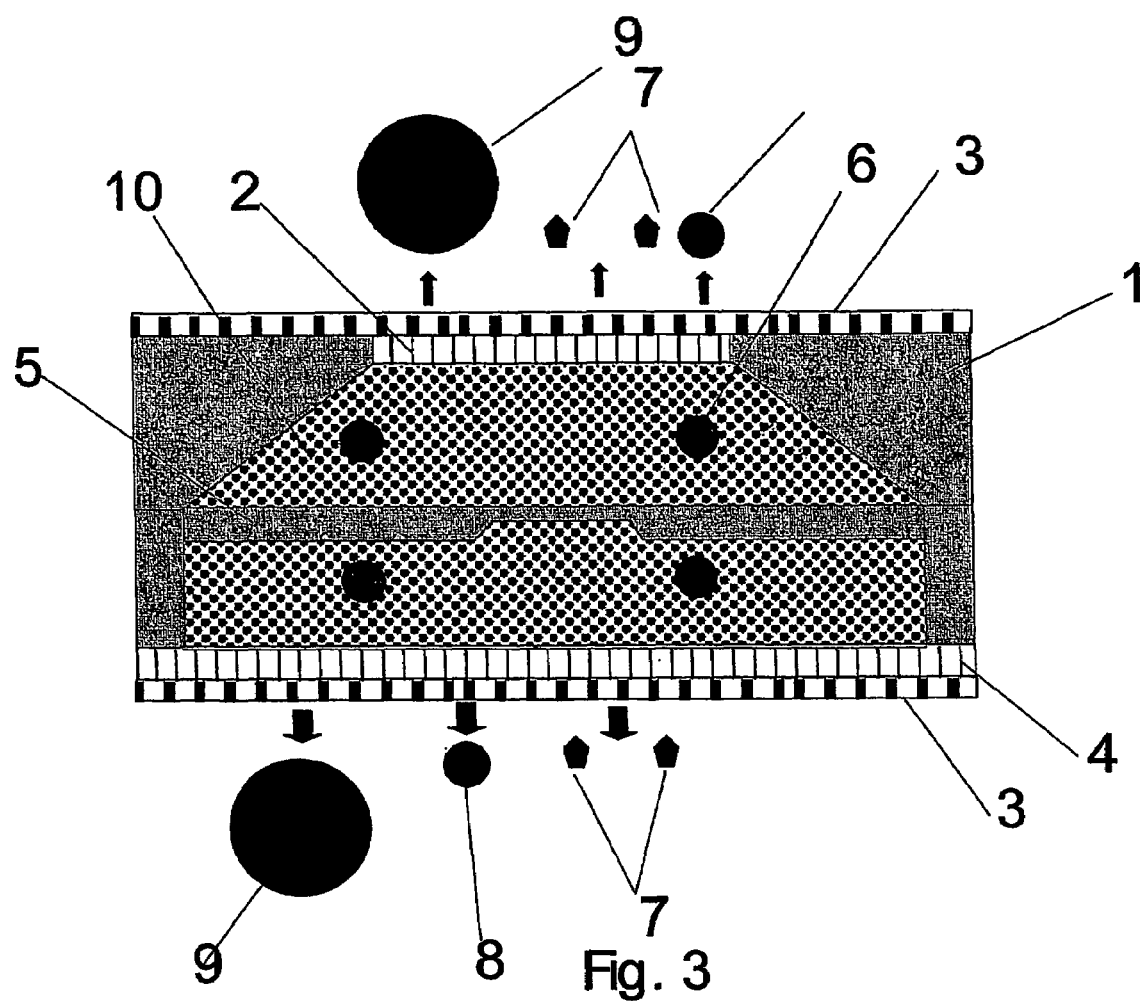
FIG. 3 illustrates another example of embodiment of the present invention.

FIG. 3 illustrates another embodiment of the present invention. The embodiment has the same elements as in the example illustrated in FIG. 2, but the area of the two membranes 2 and 4 are different.

Figure 4:
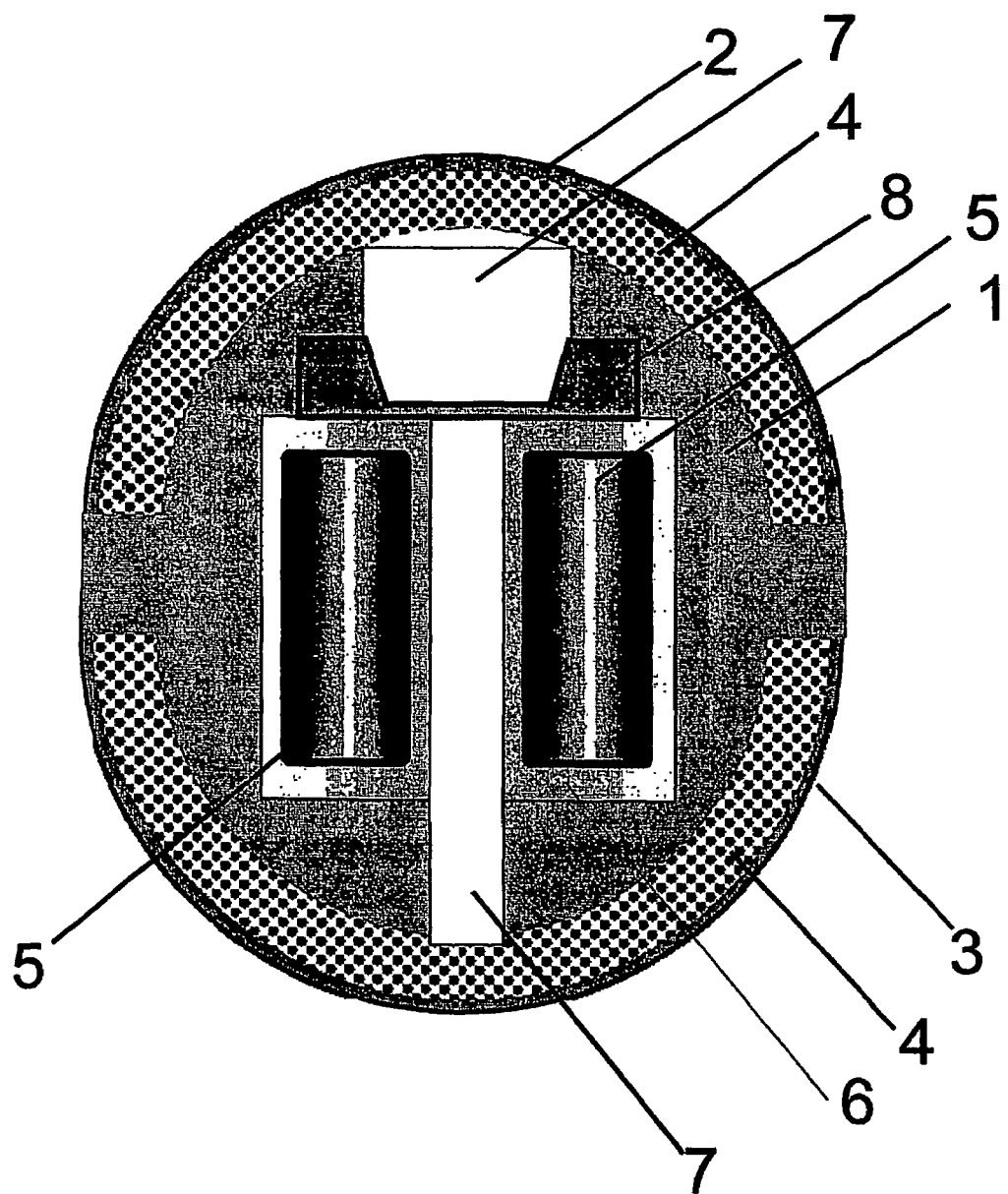
FIG. 4 illustrates an arrangement of an embodiment of the present invention.

FIG. 4 illustrates an example of arrangement of the present invention. A sensor housing 1 is machined from titan or siliconocide. In each end of the house, there are provided two half-spheres in porous metal or ceramics 4. Above each of these parts there are provided an unorganic membrane 2 and 3 with different cut-offs.

There is provided a cavity 6 n the housing 1 for the electronic circuits 5 that transforms the signals from the pressure transducers 8 to digital signals transmitted to a receiver.

The ports 7 provides communication between the pressure transducers and the reference fluids from each of the membranes 2 and 3.

Figure 5:
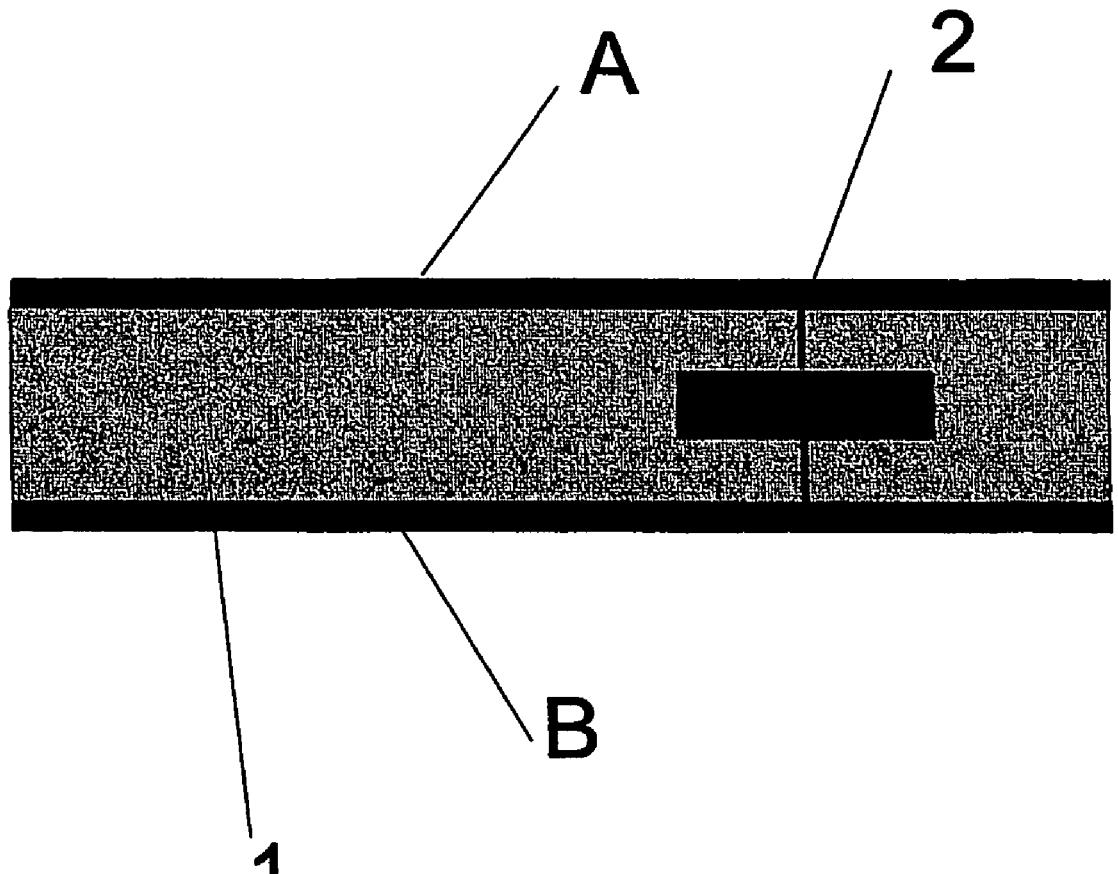
FIG. 5 illustrates another example of embodiment of the present invention.

FIG. 5 illustrates an example of embodiment of the present invention where the sensor do not provides a calibrated fluid as a reference, but two charged membranes A and B with different charges made of silicon, titan or another biocompatible material. When the ion concentration changes around the sensor, the potential between the membranes will be changed and will be proportional to the ion concentration of the body fluid.

Figure 6A:
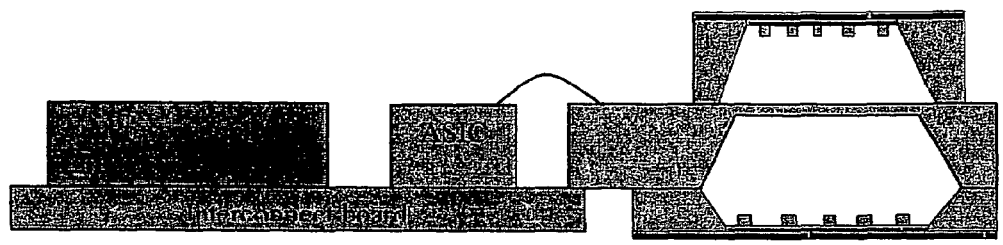
FIG. 6A illustrates a side view of an example of an embodiment of the present invention.
Figure 6B:
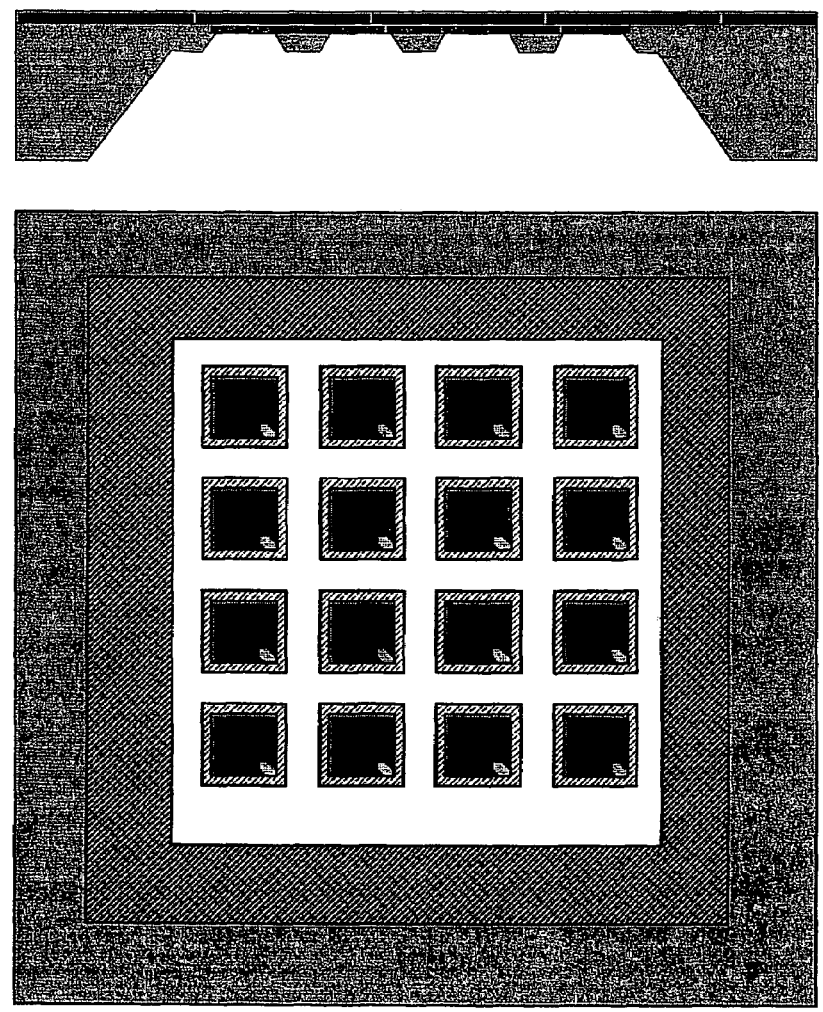
FIG. 6B illustrates a top view of the example shown in FIG. 6A.

FIGS. 6A and 6B illustrates an arrangement of a power supply, an ASIC circuit and the reference chambers according to the present invention.

The use of differential measurements is the clue to solve the problem with specificity. Differential measurements make it possible to measure the various diffusion rates (permeability) of the species that contributes to the osmotic pressure. By combining the measurements from different membranes we can therefore track the changes in concentration of the solute in question.

An additional approach is to vary the displacement versus pressure for the different reference volumes (or alternatively the available flow area). This is best done by modifying the stiffness of the osmotic membranes as described below.

Reference Fluid

The fluid inside the reference volumes, hereafter called reference fluid, is based on water, with added solutes. The type and amount of solutes is chosen to closely resemble the in vivo condition. (This fluid could for instance be Ringer Acetate). In addition to these low molecular weight electrolytes and molecules, a specific amount of a non harmful, non toxic, fully water soluble solute with a high molecular weight (>1000 Dalton) is added. This is done to ensure that the hydrostatic pressure inside the reference chambers always is higher than in the surrounding fluid. In this way, the formation of gas bubbles is avoided, which could otherwise cause a serious fail-function of the sensor.

Differential Pressure Transducer

The use of differential pressure transducers is one of the main features of the present invention. This is done to; A) Compensate for changes in hydrostatic pressure (caused by external air pressure variations, as well as tension in muscles etc.). B) Increase the resolution of the sensing elements, as the membranes of the pressure transducers are only subjected to the difference between the two osmotic pressures. As these differences are small, highly sensitive elements are designed. This increased sensitivity is important also for improving the specificity of the sensor Osmotic Membranes The semipermeable membranes are designed such that small molecules (<180 Dalton) and ions to some extent will pass through the membrane. The concentration of these substances in the reference chambers will thereby to some extent adjust to the interstitial body fluid. However, the sensor can not rely on finding the ideal membranes. The clue is membranes that have different properties with respect to the different solutes encountered in vivo.

Today there exist several techniques by which osmotic membranes can be custom-made with different properties. Examples of this are fore example "sol-gel techniques", micro perforation, etching and similar techniques giving predefined pore sizes in non-organic membranes. Alternatively organic membranes can be used. Thus it is possible to design sensors with two or more different membranes that give different responses to the different solutes in the interstitial liquid in the body. By varying only the pore size of the membrane in the range of the substance in question, but keeping the materials the same, the diffusion of the electrolytes is only slightly altered. By differential monitoring of the flux across the membranes one can therefore detect changes in the solute, which is monitored.

Beside the specifically designed pore size, the membranes also posses other important properties. These includes Preferably no (or only a small) thermal expansion missmatch with the silicon pressure sensor Ease of bonding to the silicon pressure sensor Easily defined geometrical properties as well as precisely adaptable displacement The mechanical displacement of the membrane defines accurately the amount of water that has to diffuse through the membrane to obtain a certain pressure in the reference volume. By reducing the displacement of the membrane, the response time of the element is reduced proportionally.

One way of making the osmotic membranes is to make a two-layer structure. The first layer (or substrate) is used to provide the mechanical properties of the membrane, and can typically be made by micro-machining of silicon. This technique is well known in the industry. A sufficient porosity of the thin silicon membranes formed is obtained by anodic oxidation of the silicon. This process is documented in the literature by several authors.

The "active" part of the membrane (where the osmotic properties are defined) is added as a thin film on top of the silicon substrate. This can either be a non-organic material, made for instance by a "Sol-gel" technique.

To improve the time response the water permeability must be sufficiently high. Minimising the diffusion length and maximising the pore density in the membrane support structure obtain this.

However, the sensor can easily be adapted to accept commercially available membranes of different types.

Reference Volume

The design of the reference volumes is important to obtain a high accuracy. One important factor is to minimise concentration gradients in the reference volume caused by the transport of water (or solutes) across the membrane. This is done by ensuring that the depth of the reference chambers (normal to the semipermeable membrane) is small compared to the square root of the diffusivity times the wanted response time of the element.

The reference chambers is formed in a material and with an external structure to minimise the volume displacement of the chambers when exposed to changes in hydrostatic pressure. This is important to minimise the amount of water transport through the membrane, which will increase the response time.

The reference volume is designed such that gas-bubbles are not trapped inside re-entrant cavities. This is obtained by a combination of the geometrical shape and by the choice of materials (avoid hydrophobic materials).

Filling of Reference Volume

The reference volumes are filled with a suitable solute. One alternative is to join the sensor wafer and the membrane wafers while these are immersed in the actual solution. Another alternative is to fill the reference volume through a separate filling hole, which is sealed after the filling. These two filling alternatives is performed under low atmospheric pressure (given by vapour pressure of water) to minimise the amount of air in the reference chamber.

When using a separate filling hole, the diameter of the filling hole has to be sufficient to avoid problems with surface tension induced pressures. The filling hole is plugged under liquid, and the system is designed to obtain a minimum of volume change during plugging, to avoid high pressure peeks.

If the osmotic membranes have a sufficient permeability for the low-molecular solutes (ions), filling of solvent (and low molecular weight substances) can be obtained through the osmotic membrane. The last method requires that the high molecular weight materials be deposited into the chamber before the membranes are joined to the pressure transducer. The actual filling of the "solvent" could also be performed in the body, after implantation. This can be obtained by for instance sputtering onto one or both of the parts constituting the osmotic element, not on the bonding surfaces (sputtering through a mask or Lift-off) prior to bonding.

When filling the solvent through membrane the vapour pressure inside the reference volume must be reduced compared to the external liquid (solvent) to facilitate the fling of the chamber. This is obtained by using the vapour pressure depressing effects caused by the addition of a solute in the reference volume (the high molecular weight material).

Other Materials

The invention make it possible to use silicon microelectronics whereby the sensor can be made very small and be given numerous different geometrical shapes and can thus be implanted with minute surgical operations. But, the sensor can also be produced by conventional machining technology with the only difference that the geometrical shape and size will be different.

Electrical Read-Out

The electrical signal from the pressure transducer is transformed to make it suitable for wire-less transmission to an external receiver unit. Both the coding (protocol) and the frequency is chosen to provide data integrity, security and low power consumption. Such "radio" transmission systems do partly exist today, and are also under development. The energy can either be supplied internally from a battery, or by for instance magnetic induction.

The invention claimed is:

1. Sensor for measuring a condition of body fluids comprising a sensor element adapted to be implanted in a body being in radio communication with a receiver unit outside said body, wherein said sensor element adapted to be implanted in said body comprises at least one differential pressure sensor arranged with at least two chambers, one on each side of said pressure sensor, where each chamber is confined, in one end by one side of said pressure sensor each, and on the other end by a semipermeable membrane each towards the surroundings.

2. Sensor according to claim 1, wherein said pressure sensor is arranged with piezo-electric resistor elements buried in a silicon wafer or beam.

3. Sensor according to claim 1, wherein piezo-electric resistor elements are connected as a Wheatstone bridge.

4. Sensor according to claim 1, wherein a depth for a chamber defined as the distance between said pressure sensor and said semipermeable membrane is arranged such that a gradient of a concentration of a solvent in said chamber is small.

5. Sensor according to one of the preceding claims, wherein said membranes in said sensor element are arranged sufficiently stiff to inhibit displacement of said membranes when there are changes in osmotic pressure.

6. Sensor according to claim 1, wherein said membranes are provided by anisotropic etching of a silicon wafer or a glass wafer.

* * * * *